(12) United States Patent
Haider et al.

(10) Patent No.: US 12,396,878 B1
(45) Date of Patent: Aug. 26, 2025

(54) SMART CORRECTIVE ALIGNMENT FOOT BRACE

(71) Applicant: Board of Regents of the University of Nebraska, Lincoln, NE (US)

(72) Inventors: Hani Haider, Carter Lake, IA (US); Matthew Halanski, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 395 days.

(21) Appl. No.: 17/938,163

(22) Filed: Oct. 5, 2022

Related U.S. Application Data

(60) Provisional application No. 63/252,408, filed on Oct. 5, 2021.

(51) Int. Cl.
*A61F 5/14* (2022.01)

(52) U.S. Cl.
CPC ...................... *A61F 5/14* (2013.01)

(58) Field of Classification Search
CPC ............ A61F 5/3715; A61F 2005/0197; A61F 5/0193; A61F 5/14; A43B 5/04
See application file for complete search history.

(56) References Cited

U.S. PATENT DOCUMENTS

| | | | | |
|---|---|---|---|---|
| 4,495,943 A | * | 1/1985 | Kurtz | A61F 5/0193 602/23 |
| 8,384,551 B2 | * | 2/2013 | Ross | A61B 5/6831 600/595 |
| 10,595,748 B2 | * | 3/2020 | Kubiak | A61B 5/746 |
| 10,959,484 B1 | * | 3/2021 | Tarlton | A63C 5/04 |
| 2014/0062703 A1 | * | 3/2014 | Purks | G01P 15/18 340/573.1 |

OTHER PUBLICATIONS

Morgenstein, Aaron et al. "A randomized clinical trial comparing reported and measured wear rates in clubfoot bracing using a novel pressure sensor." Journal of pediatric orthopedics vol. 35,2 (2015): 185-91.

Sangiorgio, Sophia N et al. "The Objective Measurement of Brace-Use Adherence in the Treatment of Idiopathic Clubfoot." The Journal of bone and joint surgery. American volume vol. 98,19 (2016): 1598-1605.

* cited by examiner

*Primary Examiner* — Ophelia A Hawthorne
(74) *Attorney, Agent, or Firm* — Shumaker & Sieffert, P.A.

(57) ABSTRACT

A corrective alignment foot brace is disclosed with a sensor system that allows for objective assessment and dynamic adjustment of foot brace parameters. In preferred embodiments, the corrective alignment foot brace includes a first shoe and a second shoe connected by a bar or any rigid system between them. The first shoe is configured to be adjustably oriented relative to the second shoe and relative to the bar. In some embodiments, the second shoe is similarly configured to be adjustably oriented relative to the first shoe and the bar. The corrective alignment foot brace further includes a sensor module coupled to the first shoe, the second shoe, and/or the bar. The sensor module is configured to detect at least one force or moment acting on the sensor module along or about at least one axis.

19 Claims, 16 Drawing Sheets

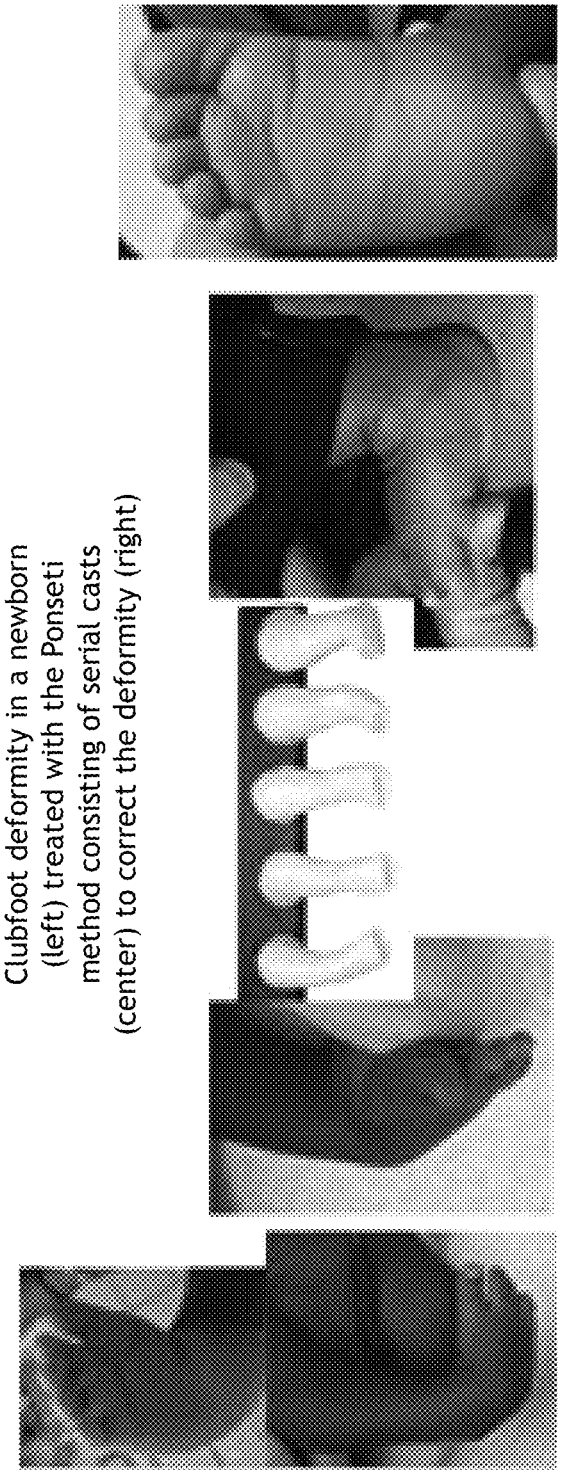
FIG. 1 Clubfoot deformity in a newborn (left) treated with the Ponseti method consisting of serial casts (center) to correct the deformity (right)

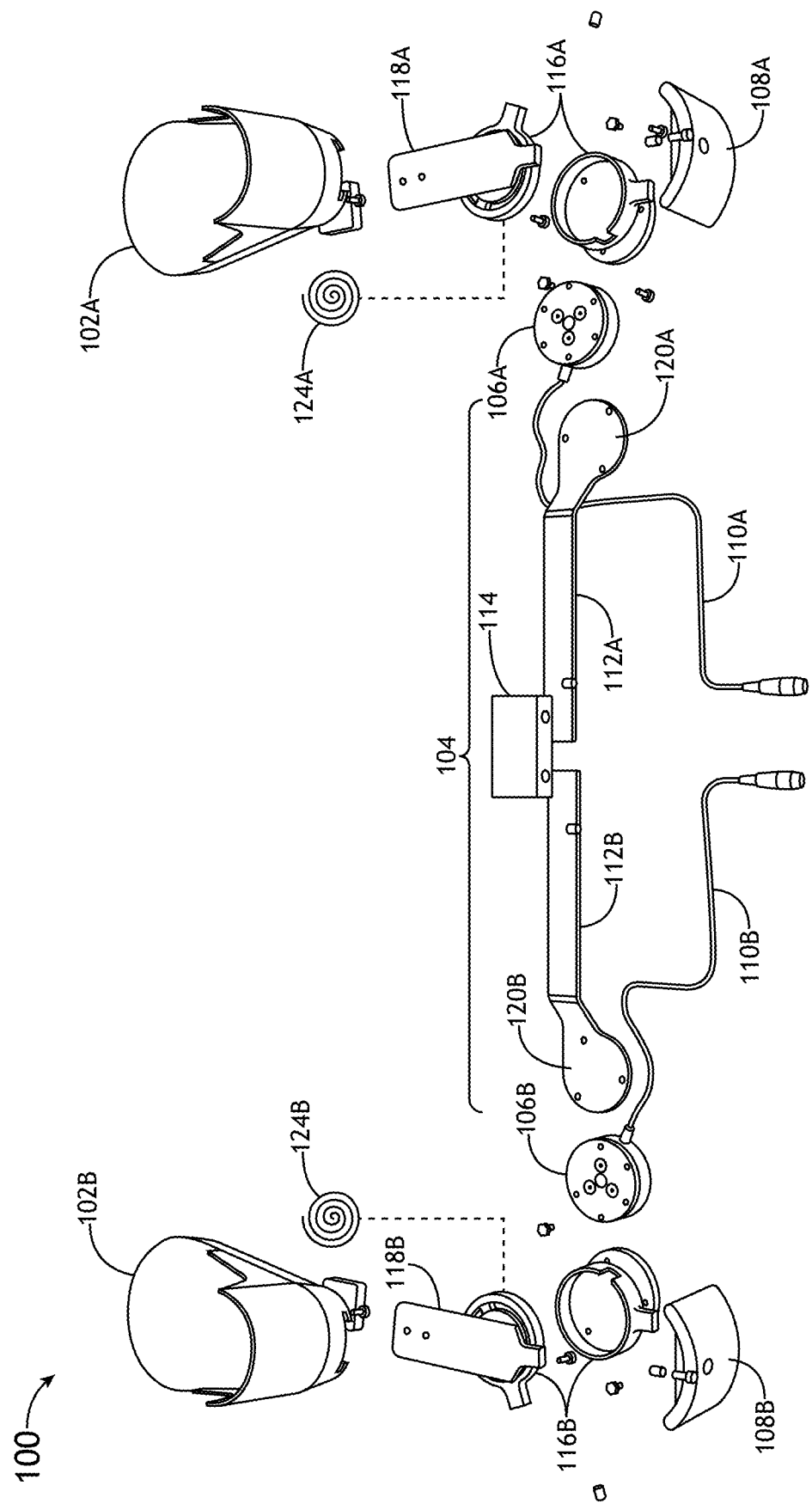

| Configuration (model) | | 3c | 4a |
|---|---|---|---|
| Model description | Load cells used | two 6 DOF load cell (between bar and shoes) | |
| | Bed support to: | Bar | Shoes |
| | Offset of supports in x-direction (a) | Considered | |
| | Offset of supports in other directions | set to 0 | |

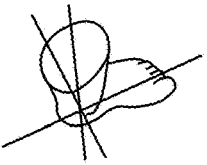

Left and/or right 6 DOF load-cells either between the shoe and bar, or below the bar

| | | 3c | 4a |
|---|---|---|---|
| Forces transmitted from left and right leg | Lx and Rx | | |
| | Ly and Ry | | |
| | Lz and Rz | | |
| Moments transmitted from left and right leg | MLx and MRx | | |
| | MLy and MRy | | |
| | MLz and MRz | | |
| Forces from left and right leg | BLx and BRx | | |
| | BLy and BRy | | |
| | BLz and BRz | | |
| Forces in bar | Sx | * | |
| | Sy | * | |
| | Sz | * | |
| Moments in bar | MSx | * | |
| | MSy | * | |
| | MSz | * | |
| Summarized results | All forces from feet | | |
| | All moments from feet | | |
| | All forces in bar | | |
| | All moments in bar | | |

FIG. 9A

SMART CORRECTIVE ALIGNMENT FOOT BRACE

CROSS-REFERENCE TO RELATED APPLICATIONS

The present application claims priority under 35 U.S.C. § 119 (e) to U.S. Provisional Application Ser. No. 63/252,408, filed Oct. 5, 2021, and titled "Crawford Smart Clubfoot Brace and Relapse Assessment Device," which is incorporated herein by reference in its entirety.

TECHNICAL FIELD

The present invention generally relates to medical devices, more specifically to corrective alignment foot braces.

BACKGROUND

Corrective alignment foot braces may be utilized for rehabilitation and to correct certain musculoskeletal disorders, such as clubfoot. Clubfoot is a birth defect/deformity in which the foot appears twisted out of shape or position, mostly where the foot appears turned inwards, sometimes to an extent where the bottom of the foot faces sideways or even upward. For example, FIG. 1 shows examples of clubfoot deformities and serial casts that can be used to induce corrective action such as implementing of the Ponseti method.

The Ponseti method, preferably implemented with a brace to constrain feet into proper alignment, has revolutionized care and drastically limited the amount of surgery needed to be performed for treatment. However, corrective alignment foot braces are currently limited in their efficacy. Individuals that cannot tolerate braces or are non-compliant with brace-wear have a significant increased risk of recurrence, and there is no simple clinical tool to determine who suffers a recurrence. It is also difficult for healthcare providers to objectively assess whether treatment is being provided at an optimal rate. The current standard is to treat all patients under the same or very similar protocol based primarily on manual assessments, periodic X-ray scans, and subjective measures of a patient's tolerance to the foot brace. In some cases, an overly aggressive corrective alignment treatment may result in non-compliance or increased risk of fracture. On the other hand, an overly conservative corrective alignment treatment may result in slow progress (hence increased length of brace-wear) when a patient could have had a shorter course of treatment.

It may be possible to improve brace-wear compliance, reduce risk of fracture, and/or optimize the course of corrective alignment treatment by objectively assessing and optimally setting, or even dynamically adjusting foot brace parameters to meet a patient's needs.

SUMMARY

A corrective alignment foot brace is disclosed with sensory electronics that allow for objective assessment and dynamic adjustment of foot brace parameters. In embodiments, the corrective alignment foot brace includes a first shoe and a second shoe rigidly or semi-rigidly connected by a bar. The first shoe is configured to be adjustably oriented relative to the second shoe and relative to the bar. In some embodiments, the second shoe is similarly configured to be adjustably oriented relative to the first shoe and the bar. The corrective alignment foot brace further includes a sensor module coupled to the first shoe, the second shoe, and/or the bar. The sensor module is configured to detect at least one force or moment acting on the sensor module along or about at least one axis. In some embodiments, the corrective alignment foot brace further includes a second sensor module (e.g., one sensor module for each shoe). However, one sensor is capable of collecting some information associated with the forces applied to either shoe from external forces (e.g., forces applied by the patient) or from the shoes acting on one another through the bar.

The data collected by the sensor module can be used to assess the patient's interaction with (or reaction to the constraints of) the foot brace. For example, low measurements of force or moment at the sensor module may be associated with patient comfort, but if these measurements are too low, then the foot brace parameters may be too relaxed and ineffective. Conversely, high measurements of force or moment at the sensor module may be associated with effective treatment. However, if these measurements are too high, then the foot brace parameters may be causing excessive patient discomfort or putting the patient at risk of fracture.

Not only the static (steady-state) values of the forces and moments would yield such information, but their dynamic (time-dependent or time-varying) behavior. For example, low almost static forces may represent a child calm and asleep, while erratic fast changing and high forces and moments may represent a child fighting to resist the brace, and there is a full spectrum in between.

The sensor module assists in quantifying the patient's physical resistance to the foot brace. In turn, the quantified results can be used to make measured adjustments to the foot brace (e.g., shoe orientation, stiffness/tension parameters, etc.).

In simpler embodiments, the corrective alignment foot brace includes a shoe that can be adjustably oriented in terms of its alignment relative to any anchoring mechanism (e.g., a bar, platform, leg brace (on same or other leg), bed, etc.) with a sensor module coupled to the shoe and/or the anchoring mechanism.

Additionally, some embodiments may include elements for controlling stiffness/resilience/tension with/without any sensory electronics. For example, the corrective alignment foot brace may include one or more adjustable, tunable or interchangeable stiffness elements with selected stiffness or tension parameters, the one or more tunable or interchangeable stiffness elements configured to act on a shoe and/or anchoring mechanism.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is provided with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 1 shows examples of clubfoot deformities and an example of a treated foot with an existing method of treatment.

FIG. 5 is another exploded view of a corrective alignment foot brace with sensory electronics, further including tunable or interchangeable stiffness elements for adjusting foot brace stiffness/resilience/tension parameters, in accordance with one or more embodiments of this disclosure.

FIG. 9A is a table showing results of an analysis performed of various configurations of modeled embodiments of a corrective alignment foot brace with sensory electronics showing what is calculable/computable and thus deterministic form the most highly equipped two configurations and what is not. Similar analysis has been done on simpler systems with one or more simpler (less degree of freedom) sensors.

DETAILED DESCRIPTION

Figure 2A:
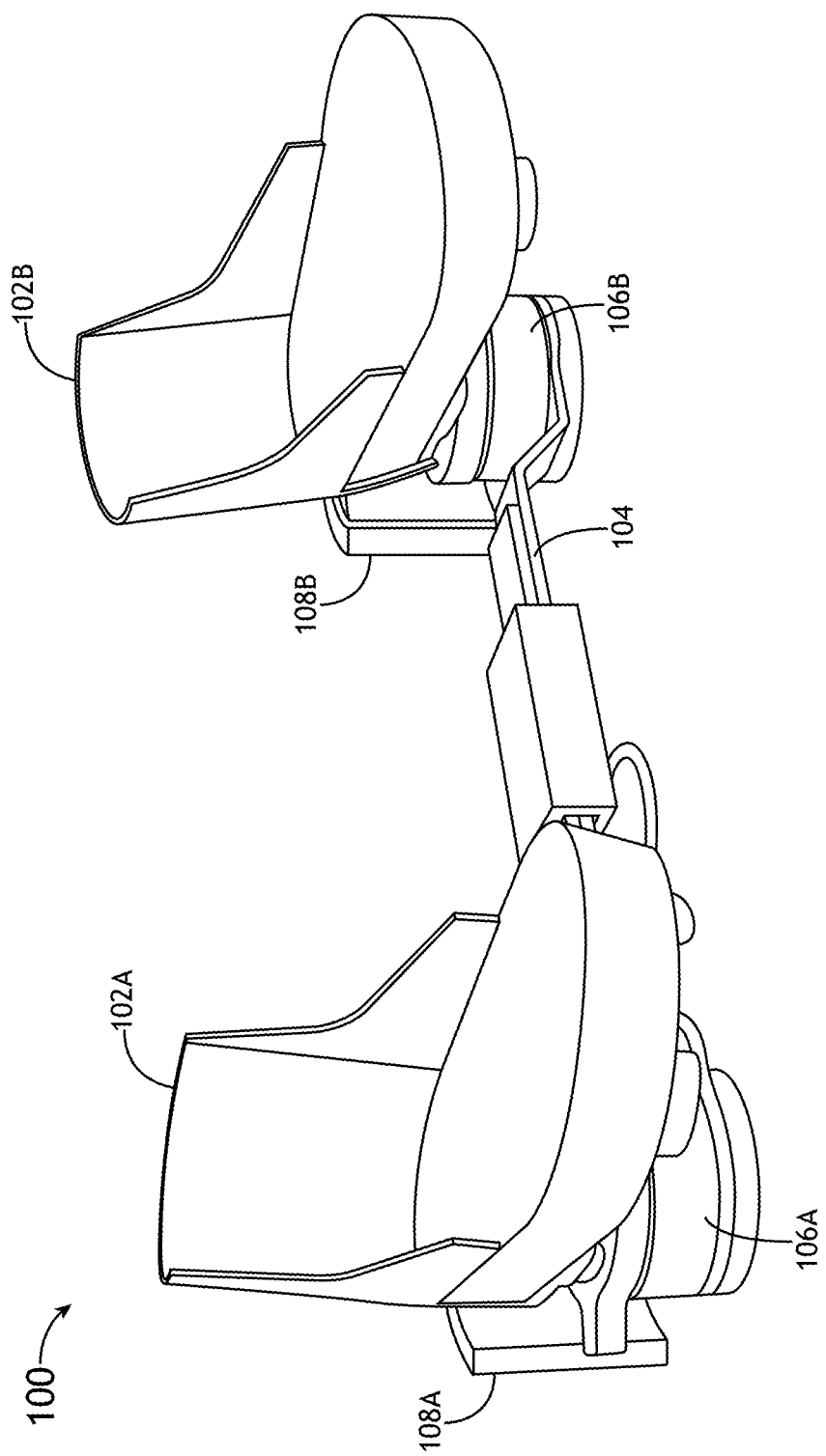
FIG. 2A is a front perspective view of a corrective alignment foot brace with sensory electronics, in accordance with one or more embodiments of this disclosure.

FIGS. 2A through 8 illustrate example embodiments a corrective alignment foot brace with sensory electronics, hereinafter referred to as the "smart foot brace 100." The smart foot brace 100 may be used to treat musculoskeletal deformities, such as clubfoot.

Clubfoot is a birth defect/deformity in approximately $1/1000$ infants in which the foot appears twisted out of shape or position, mostly where the foot appears turned partly or significantly inwards, sometimes to an extent that the bottom of the foot faces sideways or even upward.

Clinical and surgical treatment aims to correct the alignment of the foot in one or more surgical procedures followed by rehabilitation by physical constraining of the foot into gradually more accurate alignment with the growth of the child's lower limb.

The Ponseti method of treating clubfeet in infants has revolutionized care and drastically limited the amount of surgery which needs to be performed. Preferably, the Ponseti method utilizes a brace to constrain the feet into proper alignment. Affected children are recommended to wear braces until the age of 4 following treatment. Patients that cannot tolerate braces or are non-compliant with brace wear have a significant increased risk of recurrence. While several clinical parameters have also been identified as predictive of recurrence, there is no simple clinical tool to determine who gets a recurrence. For clinical diagnosis and feedback during treatment, the smart foot brace 100 can measure and alert about several factors found to be predictive of recurrence, simply, without radiation, in hopes of identifying recurrent patients at younger ages and determine when a child may be able to quit wearing the smart foot brace 100. The measurements and alerts are also intended to help the health caregiver to adjust various configurations and parameters of the brace like the level of constraint/corrective action) to optimize the treatment.

The principle of operation of the smart foot brace 100 is based on having single or multiple degree of freedom (DOF) force and/or moment measurements through sensors on the brace. An instrumented brace as such, provides feedback to the clinician or parent, about how much the resistance of the brace is, the forces the feet are applying or reacting to each other, and thus feedback as to whether the brace is being effective, perhaps offering too harsh of a constraint causing too much pain or frustration of the child, or the opposite and whether it is still needed, and the kind of adjustments needed to it which may help the treatment. In advanced configurations, the smart foot brace 100 can also be equipped with an alert system and wired or wireless communications for the feedback to be transmitted to multiple sources including through the internet to the clinical or for data from it to be processed, logged, and stored onboard the smart foot brace 100 for later communications.

An active version of the smart foot brace 100 does not only sense and provide feedback as discussed above—the smart foot brace 100 may further include means for motorized or otherwise actuated self-adjustment of the brace's own dimensions and/or stiffnesses in various directions to accommodate changes in a patient's situation as treatment progresses in time, or more dynamically in response to and/or to temporarily relieve a patient's discomfort.

Applications of the smart foot brace 100 are several fold: (1) it can be used for clinical and research purposes to screen clubfoot children for recurrence, before recurrence occurs; (2) It can be used clinically to alert families and clinicians when brace problems were occurring; (3) it can guide duration of treatment and be used to develop different protocols for different feet; (4) It can aid in differentiating non-compliance from intolerance; and (5) an advanced, adjustable stiffness version of the device can be used to remotely and/or automatically alter (the brace) treatment based on telemetry data without having to visit the clinical caregiver.

Current devices do not actually measure when the brace is on the child's feet. In other words, the effectiveness or results can only be assessed through the incremental or final clinical outcome. As such, very little improvement in the way these feet are managed either from a time in brace standpoint, brace design, foot placement, efficiency in treatment, or duration of brace treatment has been established. For example, a conventional brace prescribed in a certain configuration for 6 months wear may be effective early in treatment, say the first two months, and for the remaining four months the brace may have no functional corrective role except offering drastic curtailment of motion freedom for a suffering child, and parents too. In this example scenario, the smart foot brace 100 would have condensed the treatment in time and cost and relieved prolonged suffering. The reverse is true, as a conventional brace may be perceived to be only harsh at the start and it becomes easier as the child responds to treatment, yet the overly harsh constraint can persist for long. The smart foot brace 100 measures, to quantify and communicate such harsh constraint for it to be relieved quickly, or at least intermittently during or off child sleep times, etc.

The smart foot brace 100 lets the clinician know when the brace was functioning correctly, when the patient was having issues, how to most efficiently brace the foot, and may guide the clinician in determining when treatment is no longer necessary or can be accelerated to the next stage or attenuated for more tolerance.

The smart foot brace 100 may be implemented as a Ponseti-style clubfoot brace with one or more sensor modules configured to measure forces exerted by one foot or each foot to the brace, and vice versa, forces exerted by the feet to each other, external forces from a bed or floor, a subset or all of the forementioned forces, and any other internal/external forces acting on the brace. Although the smart foot brace 100 is described in the context of a Ponseti-style club foot brace, the smart foot brace 100 may also be implemented in the form of any other type of similarly structured corrective alignment foot brace even involving one shoe on one foot only.

Example embodiments of the smart foot brace 100 are discussed below with reference to FIGS. 2A through 8. Those skilled in the art will appreciate that the embodiments illustrated in FIGS. 2A through 8 are specific examples that can be modified by changing dimensions, rearranging components, adding/removing non-essential components or fillers, and/or replacing components with functional equivalents. Furthermore, two or more embodiments (or portions thereof) can be combined to achieve an additional embodiment that is not necessarily shown or described with reference to one drawing. As such, the drawings should not be construed as restrictive of any particular embodiment and are intended instead as visual aids to help describe configurations of certain components that may apply to multiple embodiments of the smart foot brace 100.

Figure 2B:
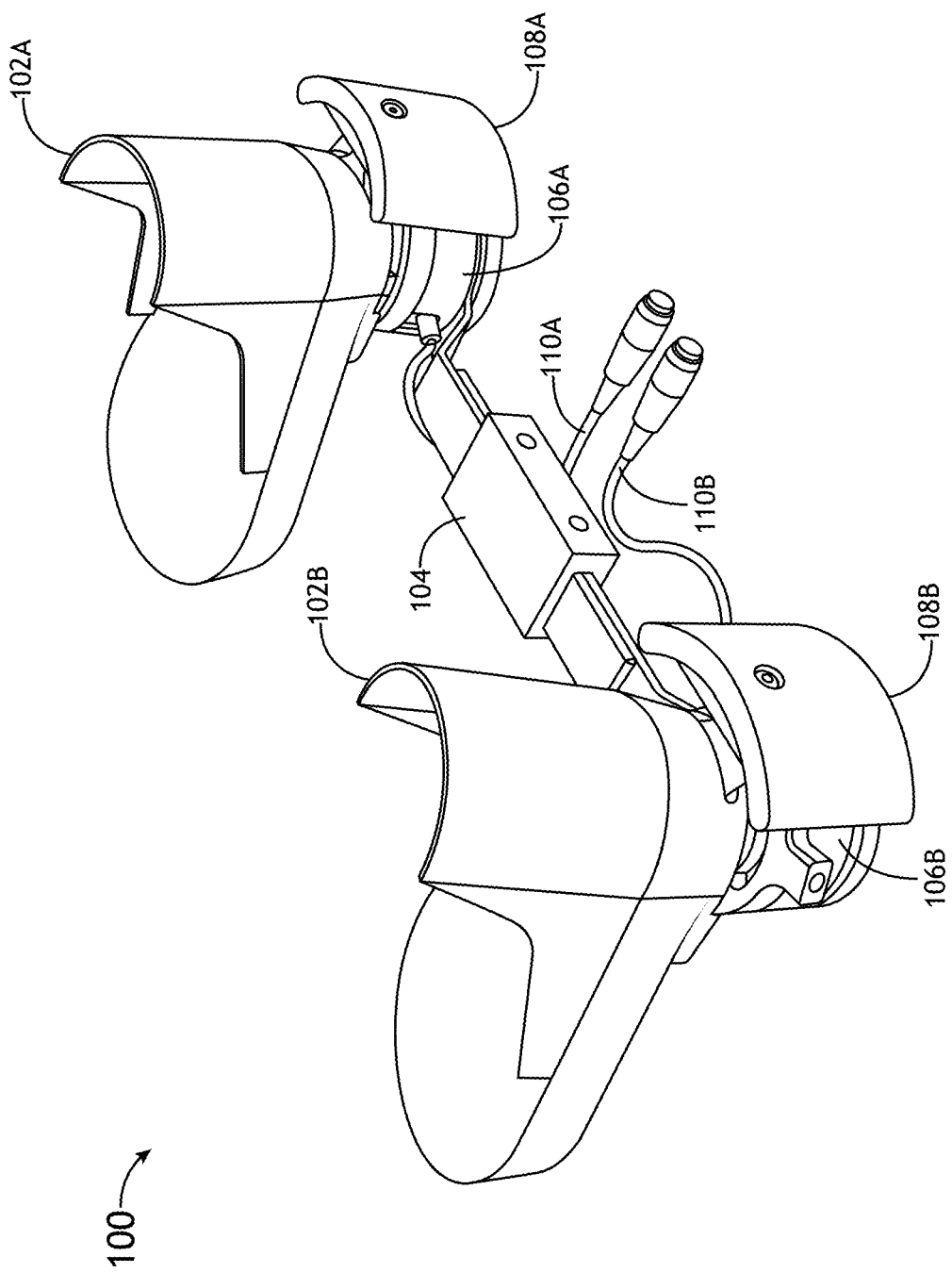
FIG. 2B is a rear perspective view of the corrective alignment foot brace of FIG. 2A, in accordance with one or more embodiments of this disclosure.

Referring now to FIGS. 2A and 2B, preferred embodiments of the smart foot brace 100 include two shoes, a first shoe 106A and a second shoe 106B, rigidly or semi-rigidly connected by a bar 104. The first shoe 106A is configured to be adjustably oriented relative to the second shoe 106B and relative to the bar 104, thereby it is an adjustable corrective clinical alignment relative to the child's body to deform them gradually or let their foot or lower limb grow more toward normal shape/anatomy. In some embodiments, the second shoe 106B is similarly configured to be adjustably oriented relative to the first shoe 106A and the bar 104. As used herein, the term "shoe" may include an enclosed shoe, an open shoe, a sandal, a boot, or any other type of footwear or constraining or encapsulating element that can be used to constrain a foot according to a specified alignment/geometry.

In some embodiments, the smart foot brace 100 includes a first sensor module 106A coupled to the first shoe 102A and a second sensor module 106B coupled to the second shoe 102B. For example, each of the sensor modules 106A, 106B may be located underneath or in close proximity to each of the shoes 102A, 102B, respectively. Alternatively, the sensor modules 106A, 106B may be embedded within the shoes 102A, 102B. However, non-embedded configurations provide certain advantages because the (non-embedded) sensor modules 106A, 106B are capable of detecting all of the forces exerted on and by the shoes 102A, 102B instead of detecting a localized measurement of force/moment at a specific portion of a shoe.

Figure 3:
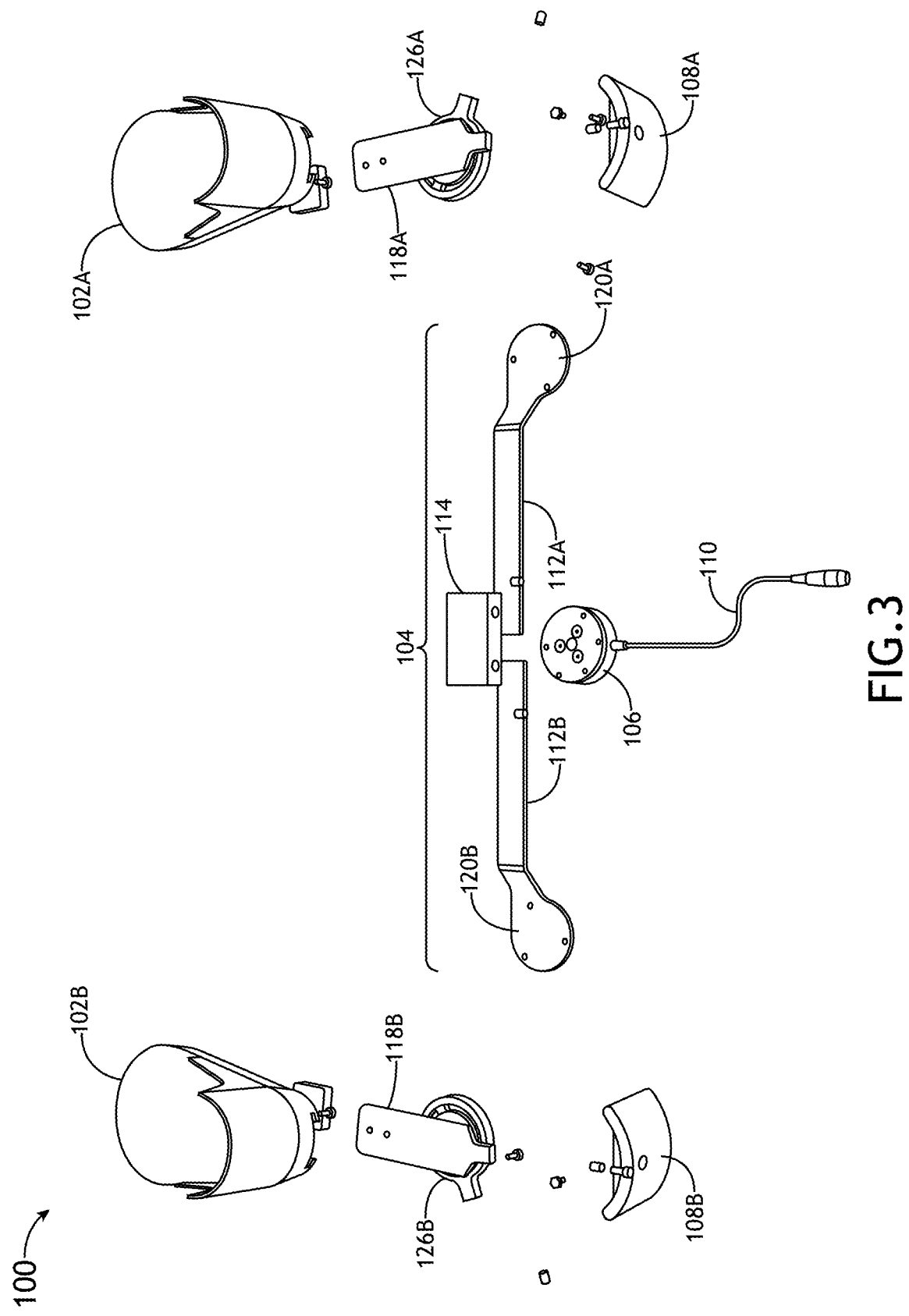
FIG. 3 is another exploded view of a corrective alignment foot brace with sensory electronics, in accordance with one or more embodiments of this disclosure.

In other embodiments, the smart foot brace 100 includes one sensor module 106A/106B coupled to one shoe 102A/102B or alternatively a sensor module 106 coupled to the bar 104 that connects the shoes 102A, 102B (e.g., as shown in FIG. 3). Even with one sensor module, the system may be able to detect aggregate measures of forces exerted by each foot to the brace, and vice versa, forces exerted by the feet to each other, external forces from a bed or floor, a subset or all of the forementioned forces, and any other internal/external forces acting on the brace. However, multiple-module configurations may be better at capturing data samples that correspond to forces exerted on/by each foot individually, in addition to the aggregate measures that can be collected through the use of a single sensor module. Extra sensors may provide some redundancy in measurements, but measuring a variable directly, or calculating its value from other measurements in the system, provides a way to check/verify and establish an estimate of uncertainty in the measurements or errors due to noise, sensor sensitivity, crosstalk between the different measurement axes, or other error sources.

Each sensor module (e.g., sensor module 106, 106A, and/or 106B) is configured to detect at least one force or moment acting on the sensor module along or about at least one axis. In advanced configurations, each sensor module comprises a multiple axis sensor configured to detect a plurality of forces or moments acting on the sensor module along or about a plurality of axes. In some embodiments, each sensor module comprises a load cell, for example a 6 DOF (or less) load-cell capable of measuring three forces along and three moments around three orthogonal axes (e.g., x, y, and z axes), or a subset of the forementioned force/moment measurements (if less than 6 DOF). The force and moment sensors can be alternatively enabled as any combination of one or more strain-gauge sensors embedded within the brace bar or any other part of the system to have them smaller, lighter, and buried/hidden for protection. Alternative to strain gauge sensors are piezo-electric based force sensors, inductive based sensors, or any other force or moment sensor technology. The purpose is to detect forces and moments transmitted or seen by the brace to represent the reactions from the child, or vice versa.

Figure 2C:
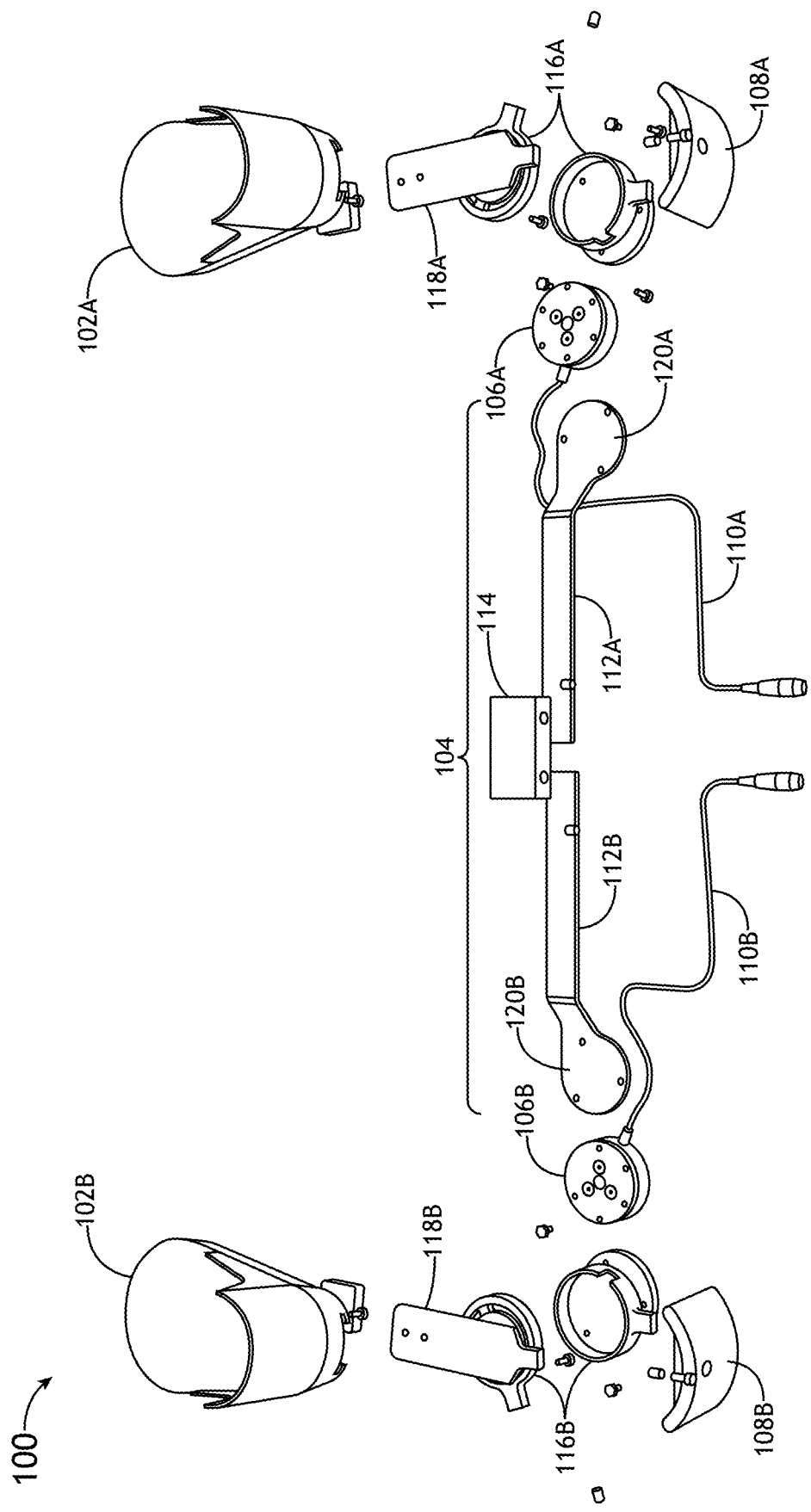
FIG. 2C is an exploded view of the corrective alignment foot brace of FIG. 2A, in accordance with one or more embodiments of this disclosure.

In some embodiments, the bar 104 has an adjustable length. For example, as shown in FIG. 2C, the bar 104 may include at least two bar members 112A, 112B held together by an adjustable coupler 114 that allows the bar members 112A, 112B to be positioned relative to one another (e.g., pushed together or pulled apart) and then fixed in the desired position. This allows the smart foot brace 100 to accommodate patients having different dimensions (e.g., different shoulder/hip widths). In other embodiments, the bar 104 may have a fixed length. In this case, differently sized patients may need to use a different brace or the bar 104 may be interchangeable with differently sized bars to accommodate differently sized patients.

The bar 104 may similarly be made out of modular elements to add or reduce stiffness to it, and thus its stiffness is adjustable. Varying the elasticity (compliance) of the bar provide means of reducing the perceived constraint and thus frustration of the child.

In multiple-module configurations, the sensor modules 106A, 106B may be coupled to the bar 104 beneath each of the shoes 102A, 102B, respectively. For example, each of the sensor modules 106A, 106B can be mounted to a corresponding attachment site on the bar 104 (e.g., attachment sites 120A, 120B). In some embodiments, the sensor modules 106A, 106B may be held within sensor cases 116A, 116B configured to provide structural support for mounting the sensor modules 106A, 106B to the attachment sites 120A, 120B on the bar 104. Each of the sensor cases 116A, 116B may comprise a lower case structure that includes a cavity for holding base member of the sensor module 106A/106B and an upper case structure that includes a second cavity for holding force-sensing plate that sits on top of the base member of the sensor module 106A/106B. The lower case structures may be configured for (directly or indirectly) fastening to the attachment sites 120A, 120B on the bar 104. The upper case structures may be configured for (directly or indirectly) fastening to the shoes 102A, 102B. The use of upper and lower case structures allows for relative motion between the shoe 102A/102B and the bar 104, said motion being relayed through movement (strain) of the force-sensing plate relative to the base member of the sensor module 106A/106B (though this movement may not be visible to the naked eye).

The sensor modules 106A, 106B or their sensor cases 116A, 116B may be directly fastened to the shoes 102A, 102B. In such configurations, the sensor modules 106A, 106B or sensor cases 116A, 116B can be mounted to the shoes 102A, 102B by fasteners (e.g., screws, clips, etc.) that must be unfastened/removed to change shoes, for instance, to accommodate different shoes sizes. In more preferred embodiments, the smart foot brace 100 includes adapters 118A, 118B that allow shoes to be interchangeably coupled/decoupled from the smart foot brace 100 more easily and with better support when the shoes 102A, 102B are secured to the smart foot brace 100. In some embodiments, the adapters 118A, 118B are coupled to or integrated within the sensor cases 116A, 116B. For example, the adapters 118A, 118B may be coupled to or integrated within the upper case structures of the sensor cases 116A, 116B. The adapters 118A, 118B may be (directly or indirectly) coupled to the sensor modules 106A, 106B in any other fashion. The adapters 118A, 118B are configured to interface with the shoes 102A, 102B, respectively, via a coupling interface that is common to a plurality of interchangeable shoes in order to accommodate different shoe sizes and designs by easily swapping in/out differently sized shoes. For example, as shown in FIGS. 2A through 5, each of the adapters 118A, 118B may include a plate that is configured to slide into a cooperatively sized slot in each shoe. Other types of cooperatively engaging interfaces may be employed (e.g., form-fit interfaces, snap-fit interfaces, threaded interfaces, ball-and-socket, pins-and-holes, etc.). For example, FIGS. 6A through 6E illustrate another embodiment of adapter 118A-adapter 118B may be similarly structured if present.

Throughout all the above, the sensor orientation with regards to the measurement axes can be made fixed constant regardless of the set rotation of the shoe relative to the bar (level of corrective action set) by the caregiver. In this way, the direction of the forces along x, y and z of the sensor remain the same regardless of the configuration of the shoe angle. This obviously makes the data processing and interpretation easier by having the forces and moments having fixed axes (directions) relative to the human body (anatomical body axes or lower limb axes). Alternatively, the sensor orientation may be selectively chosen in some configurations to be fixed relative to the shoe/foot and tilts or turns with the foot. In such a configuration, the sensor measurements are always relative to the foot which can be useful if the caregiver needs to make the measured data more pertinent to the foot in certain directions always fixed relative to the foot.

In some embodiments, the smart foot brace 100 further includes one or more configurable bed support shields (e.g., bed support shields 108A, 108B) for controlling which part of the sensor (the part attached to the bar, or the part attached to the shoe/foot) is bearing the forces between the sensor module(s) 106A, 106B, and/or 106 and a bed (or bed-like structure). This alternative setup governs what is directly measurable by the system (e.g. all the forces/moments in the bar, or all the forces/moments on the foot) in the data processing and analysis. What the bed forces are being applied to makes a difference. The one or more configurable bed support shields can either be structurally fastened to the brace assembly, or to the shoes. Depending on whether bed support shields are fastened to the brace assembly or the shoes, the bed forces and moments may be treated as part of the brace or shoe system of forces/moments. The manner in which the forces and moments are treated will affect how they are determined/computed from the sensor signals. For example, the table in FIG. 9A shows two columns, one representing a bed support shield 108A/108B on one modular element, and the other showing the analysis possible with the bed support shield 108A/108B attached to the other. Furthermore, the bed support shield design illustrated in the drawings makes it easy to have the same bed support shield 108A/108B attach in two different ways, simply by turning it upside down.

As previously mentioned, the smart foot brace 100 may include two sensor modules 106A, 106B, as in many of the configurations discussed above. Alternatively, the smart foot brace 100 may function with one sensor module. In some single-module embodiments, sensor module 106A or sensor module 106B is removed from the system. To maintain symmetry, the missing sensor module may be replaced by a filler (e.g., any structure that occupies a similar amount of space), although fillers may not be necessary as the device is typically worn while sleeping or laying down. As shown in FIG. 3, in other single-module embodiments, an identical or structurally and/or functionally similar sensor module (sensor module 106) may be coupled to the bar 104. For example, the sensor module 106 may be coupled to the bar 104 at a position in between the two shoes 102A, 102B. Here, one (e.g., top) side of the sensor would be rigidly attached to one (e.g., left) half of the bar and the other (lower) side of the sensor attached to the other (right) half of the bar. Thus, such a single sensor would directly measure all the three (x, y and z) forces transmitted through the bar and three moments around these axes and hence all the bar action can be evaluated. In this case, the shoes 102A, 102B may be coupled to the attachment sites 120A, 120B on the bar 104 directly or via mounting plates 126A, 126B and optionally with the use of adapters 118A, 118B that are coupled to the mounting plates 126A, 126B.

With one sensor module, the system can detect an aggregate measure of forces exerted by each foot to the brace in the absence of any other external forces or moments on the bar. Or this single sensor (with one or more measurement axes) can measure forces and moments exerted by the feet to each other, combined with external forces or moments from a bed or floor, and any other internal/external forces acting on the brace. Depending on the number of axes of the sensor, a subset of all these forces or moments in one or more directions can be measured. However, multiple-sensor configurations may be better at capturing data samples that correspond to forces exerted on/by each foot individually. In some embodiments, the smart foot brace 100 may include more single/multiple axis sensor modules (e.g., strain gauges embedded in the bar or the shoe adaptors) for similar data sampling.

Each of the shoes 102A, 102B (or at least one shoe) has adjustable alignment parameters. For example, each shoe may include or may be coupled to a multiple DOF platform for controlling the orientation (e.g., yaw, pitch, and/or roll) of each shoe relative to the bar 104 and/or relative to the other shoe. In some embodiments, each shoe may further include one or more mechanisms (e.g., adjustable air cushions, springs, internal supports, fasteners, etc.) for adjusting the stiffness or compliance of each shoe.

Figure 4:
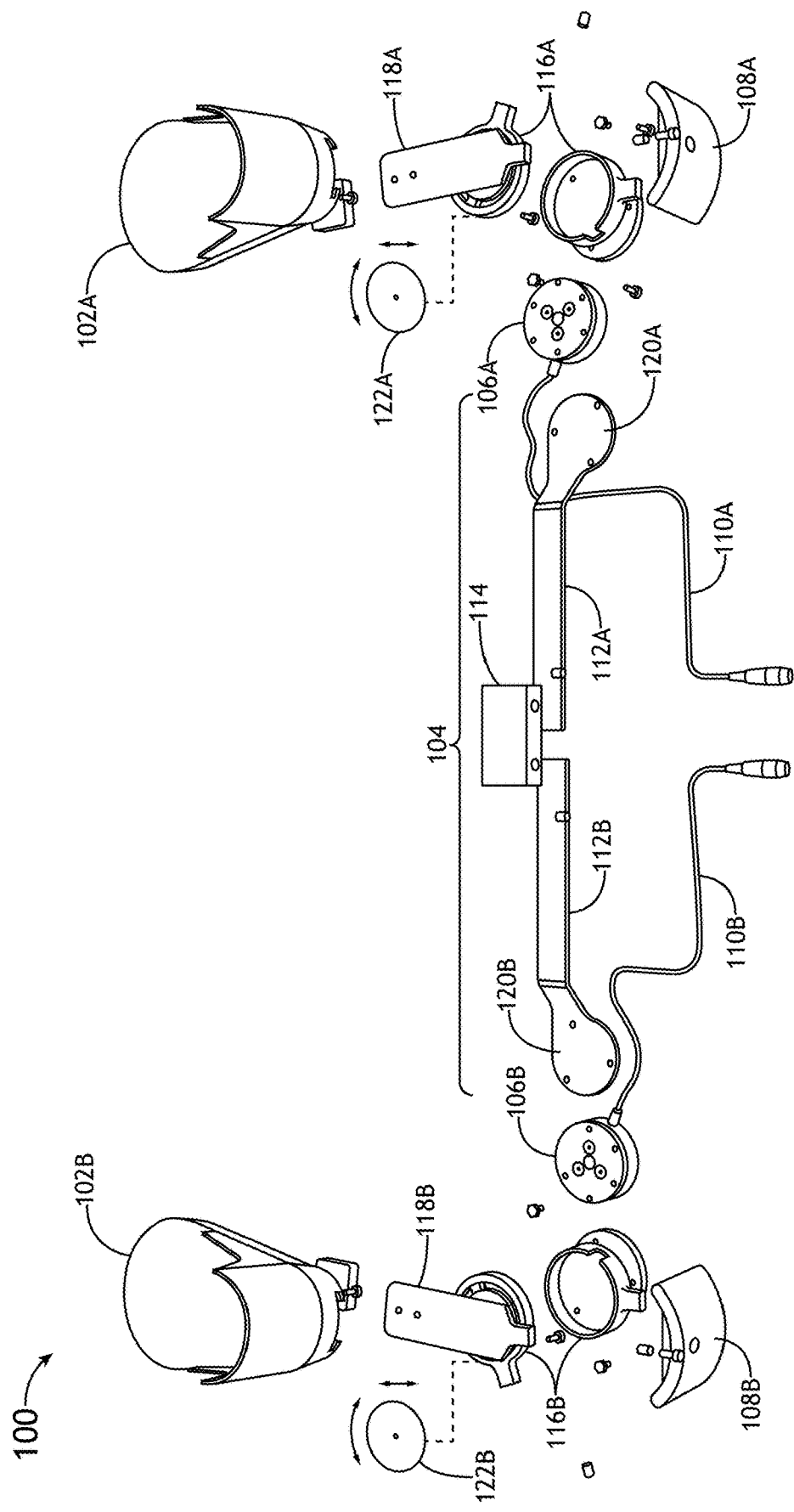
FIG. 4 is another exploded view of a corrective alignment foot brace with sensory electronics, further including one or more actuators for controlling foot brace alignment and/or stiffness parameters, in accordance with one or more embodiments of this disclosure.
Figure 6A:
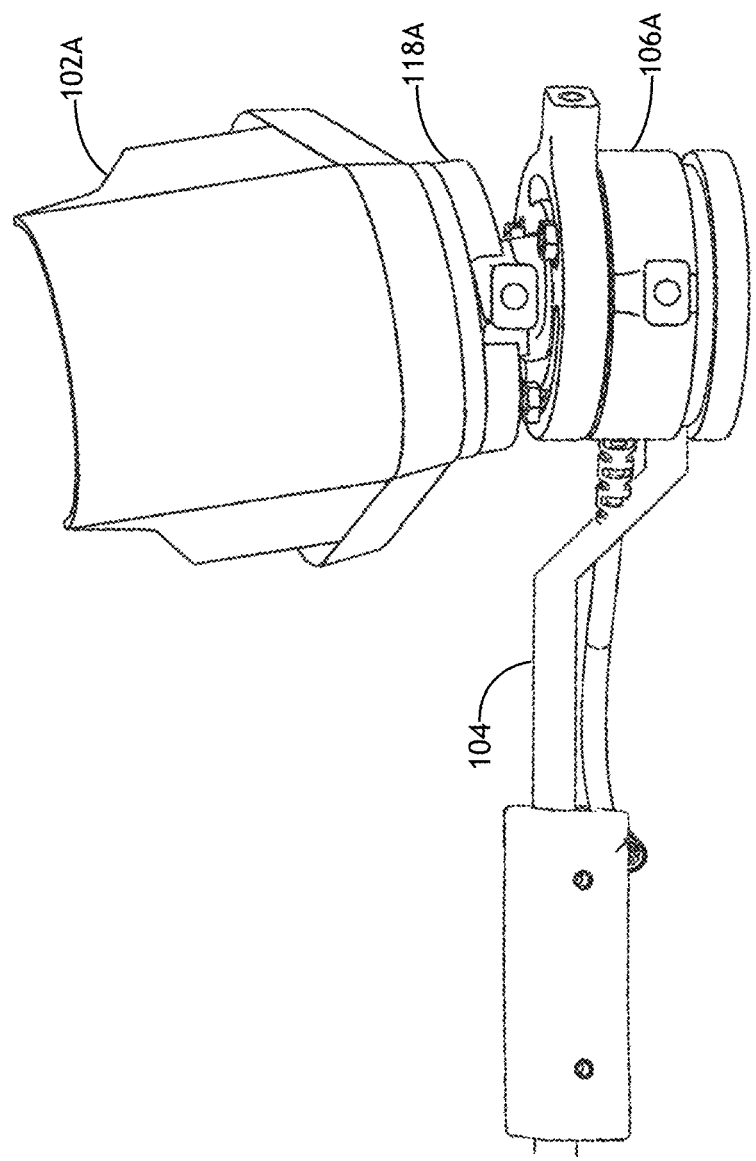
FIG. 6A is a partial rear view of a corrective alignment foot brace with sensory electronics, with a different shoe-to-brace adapter configuration than the one illustrated in FIGS. 2A through 5, in accordance with one or more embodiments of this disclosure.
Figure 6B:
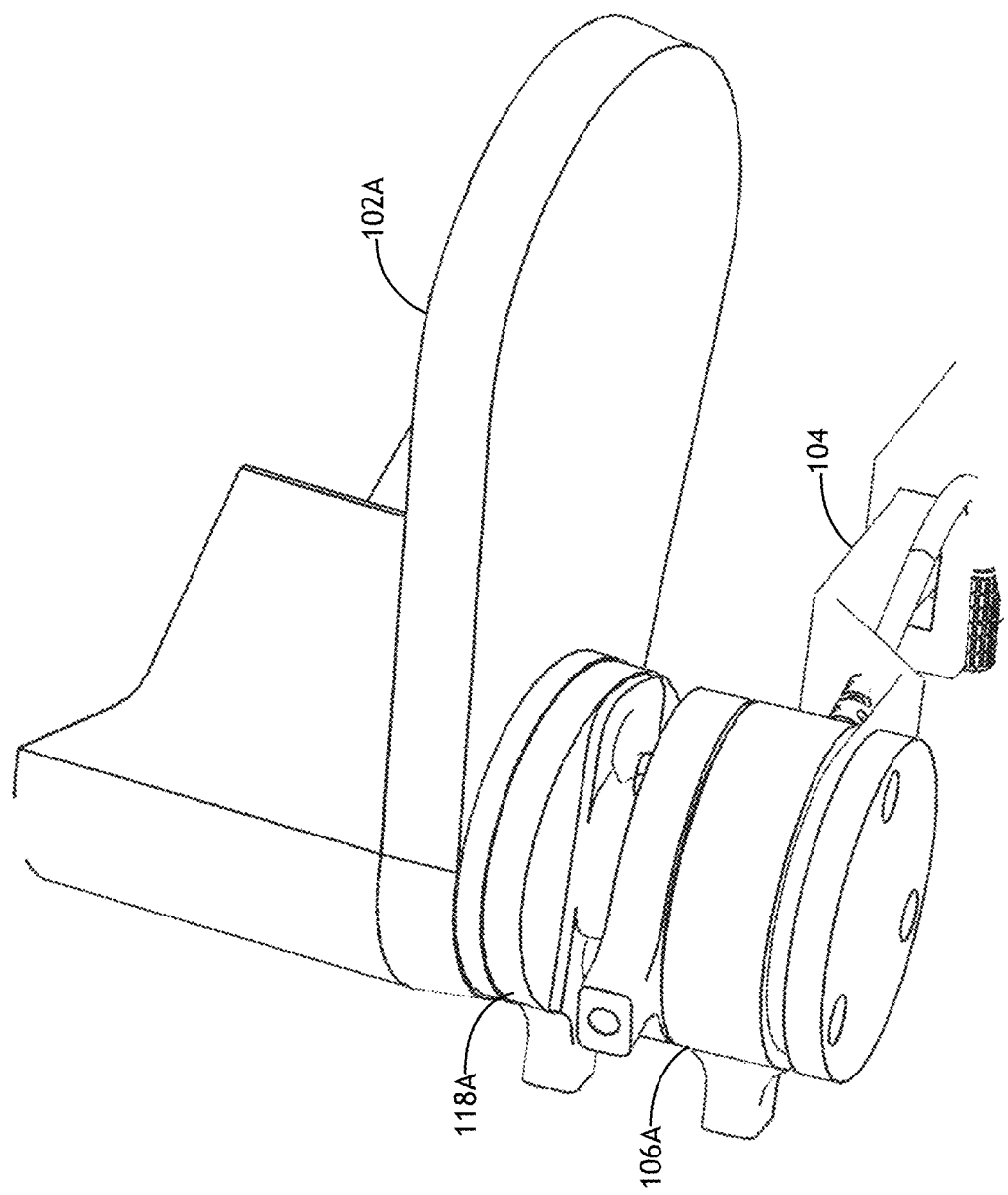
FIG. 6B is a partial front perspective view of the corrective alignment foot brace of FIG. 5, in accordance with one or more embodiments of this disclosure.
Figure 6C:
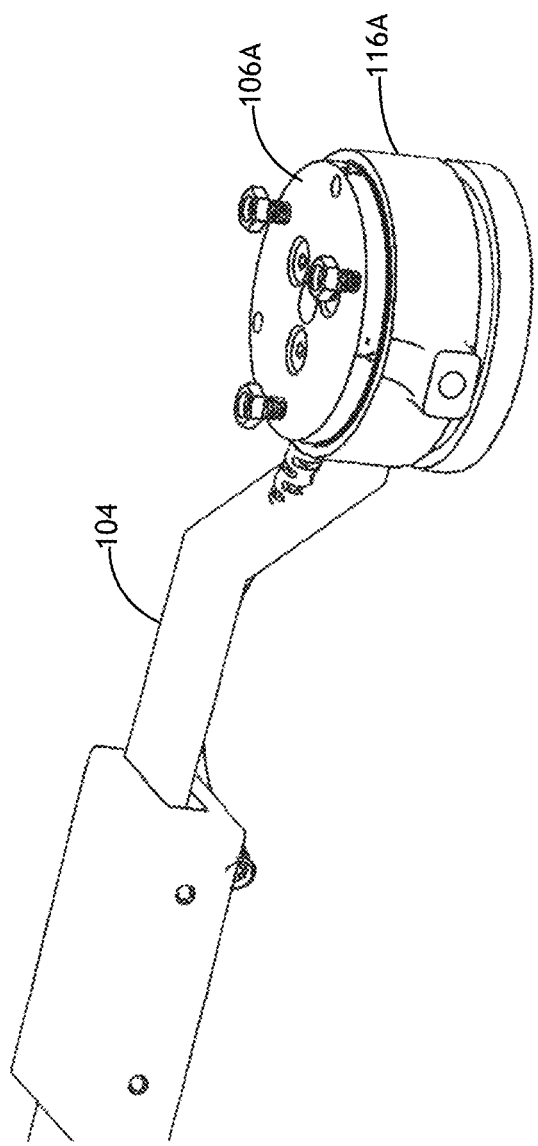
FIG. 6C is a partial rear perspective view of the corrective alignment foot brace of FIG. 5 with the adapter and a top portion of a sensor case removed to uncover a sensor module, in accordance with one or more embodiments of this disclosure.
Figure 6D:
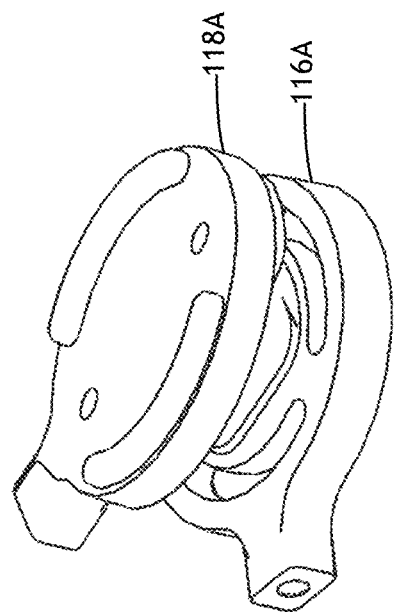
FIG. 6D is a perspective view of the adapter and the top portion of the sensor case which are removed (not shown) in FIG. 6C, in accordance with one or more embodiments of this disclosure.
Figure 6E:
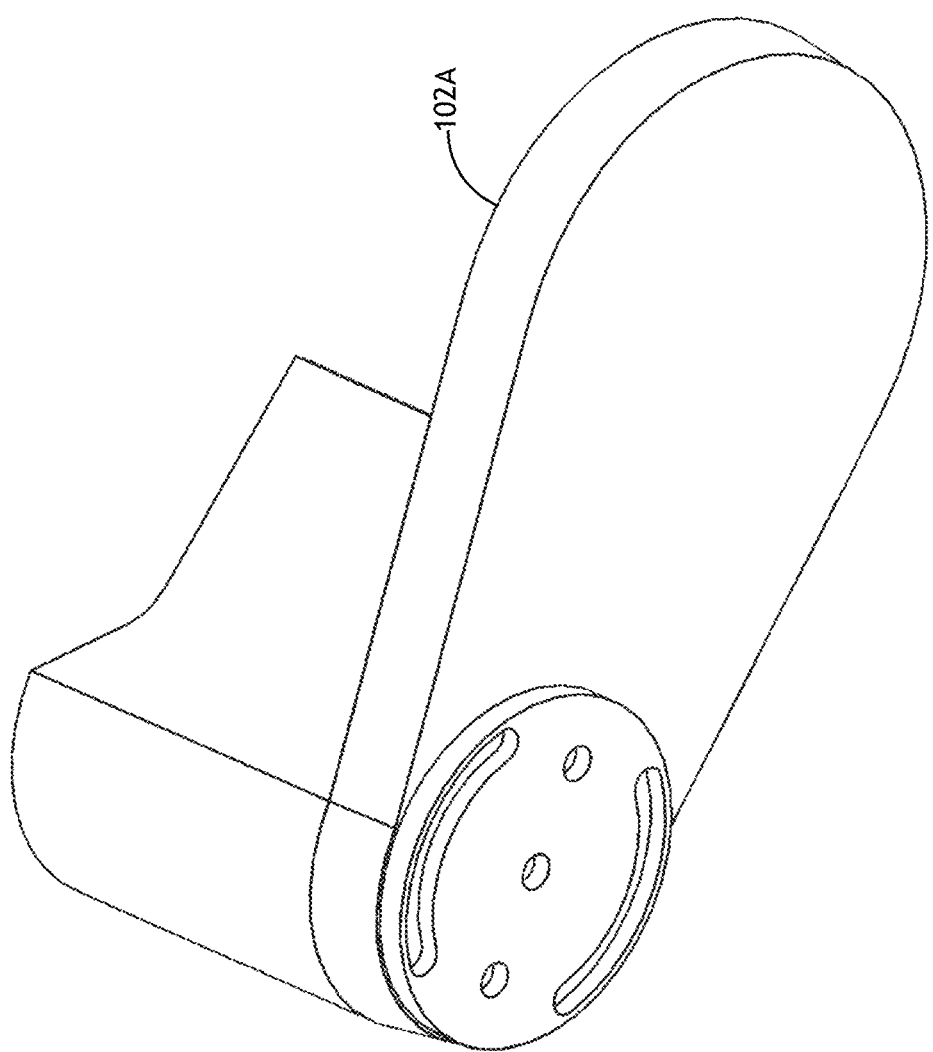
FIG. 6E is a perspective view of a shoe with a coupling interface that matches the adapter in FIG. 6D, in accordance with one or more embodiments of this disclosure.

In advanced embodiments, the smart foot brace 100 can also be equipped with a dimensional and/or stiffness changing functionality which can be either manually or remotely controlled by wired or wireless electronic signals. This capability can help adjust the dimensional setup (e.g., internal/external rotation of the shoe/foot) and/or stiffness of the brace (e.g., recruiting/engaging stiffness or compliance elements such as springs, or frictional elements, etc.) for the purpose of adjusting the brace to attenuate its constraint function (e.g., to temporarily accommodate child frustration), or amplify its function (e.g., to further correct the deformity once some corrections have occurred during treatment). For example, as shown in FIG. 4, the smart foot brace 100 may include one or more actuators 122A and/or 122B (e.g., piezo electronic linear or rotational actuators, or electric stepper or servo motors or the like) configured to orient the shoes 102A, 102B relative to the bar 104. The actuators 122A, 122B may be further configured to control stiffness by tightening shoe fasteners or moving one or more internal shoe structures.

Additionally or alternatively, the smart foot brace 100 may include one or more tunable or interchangeable stiffness elements 124A and/or 124B (e.g., torsion springs or other springs or spring-like structures), as shown in FIG. 5. In some embodiments, the bar 104 is essentially rigid but can be deliberately given some elasticity or compliance. For example, the bar 104 may be flexible or may include springs affecting the bar members 112A, 112B, and this stiffness can be made different in different directions (e.g. a bar that is stiff in length but allowed to twist with less stiffness in torsion or allowed to bend and vice versa). The stiffness of the system may in one or more directions may be adjusted by tuning or interchanging modular spring elements to control stiffness/tension parameters. In some embodiments, the tension/force applied by the smart foot brace 100 is based on measurements of force and/or moment collected by the sensor module(s) 106A, 106B, and/or 106. For example, the selected stiffness or tension parameters of the tunable or interchangeable stiffness elements 124A, 124B can be based on data collected by the sensor module(s) 106A, 106B, and/or 106. In some cases, these parameters are selected in a manner that achieves force and/or moment measurements at the sensor module(s) 106A, 106B, and/or 106 within a selected range and/or fulfilling certain selective criteria. At the same time, stiffness elements may provide some relief to the patient. For example, the patient may be capable of overcoming the applied force while awake, thereby achieving temporary non-optimum alignment; meanwhile, the patient experiences more effective constrained and corrective alignment treatment when asleep and unable to resist the brace.

Additionally, some embodiments of the smart foot brace 100 may include elements for controlling stiffness/resilience/tension without any sensory electronics (or with only a portion of the sensory electronics described herein).

Figure 7:
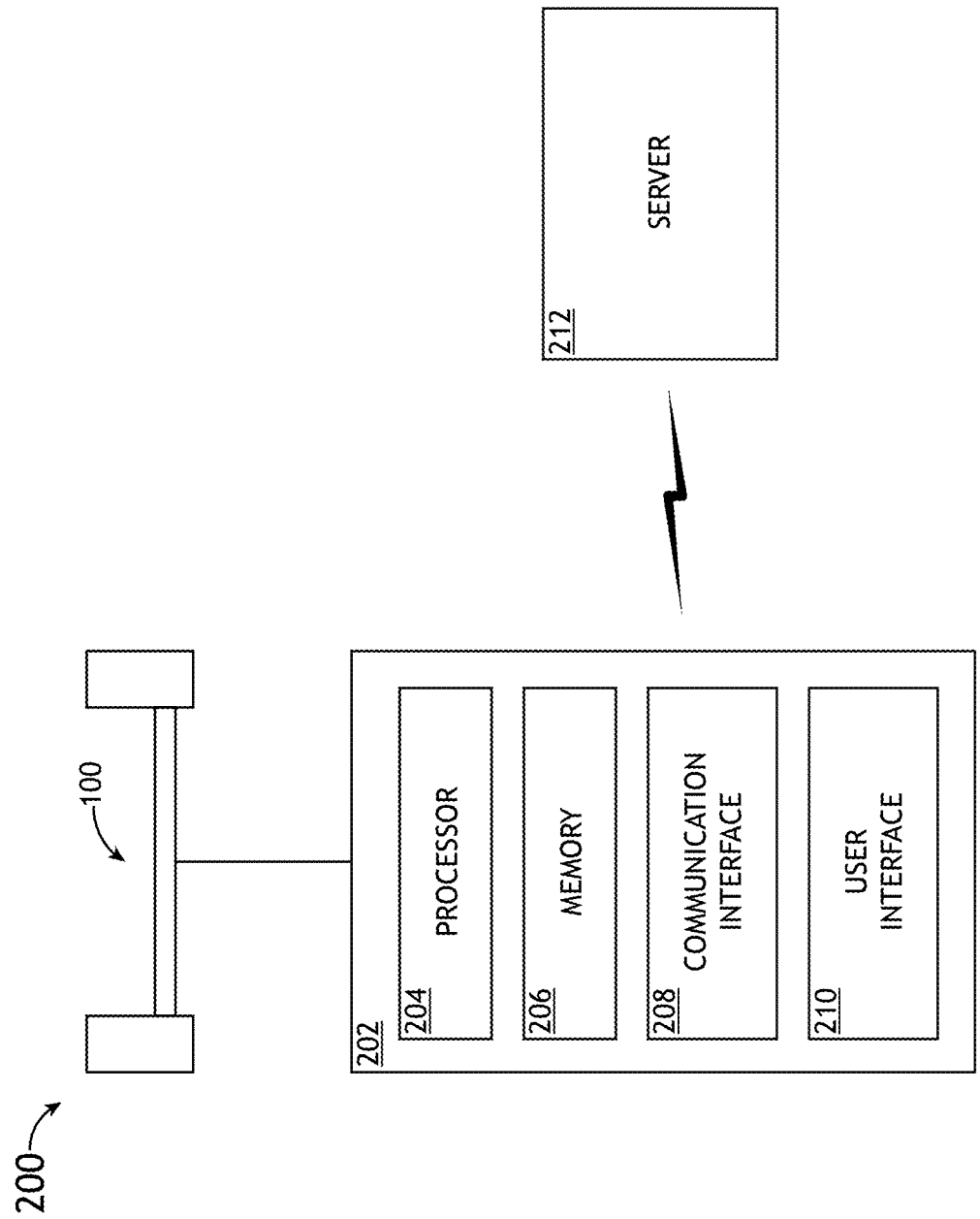
FIG. 7 is a block diagram of an information system that includes a corrective alignment foot brace with sensory electronics, in accordance with one or more embodiments of this disclosure.
Figure 8:
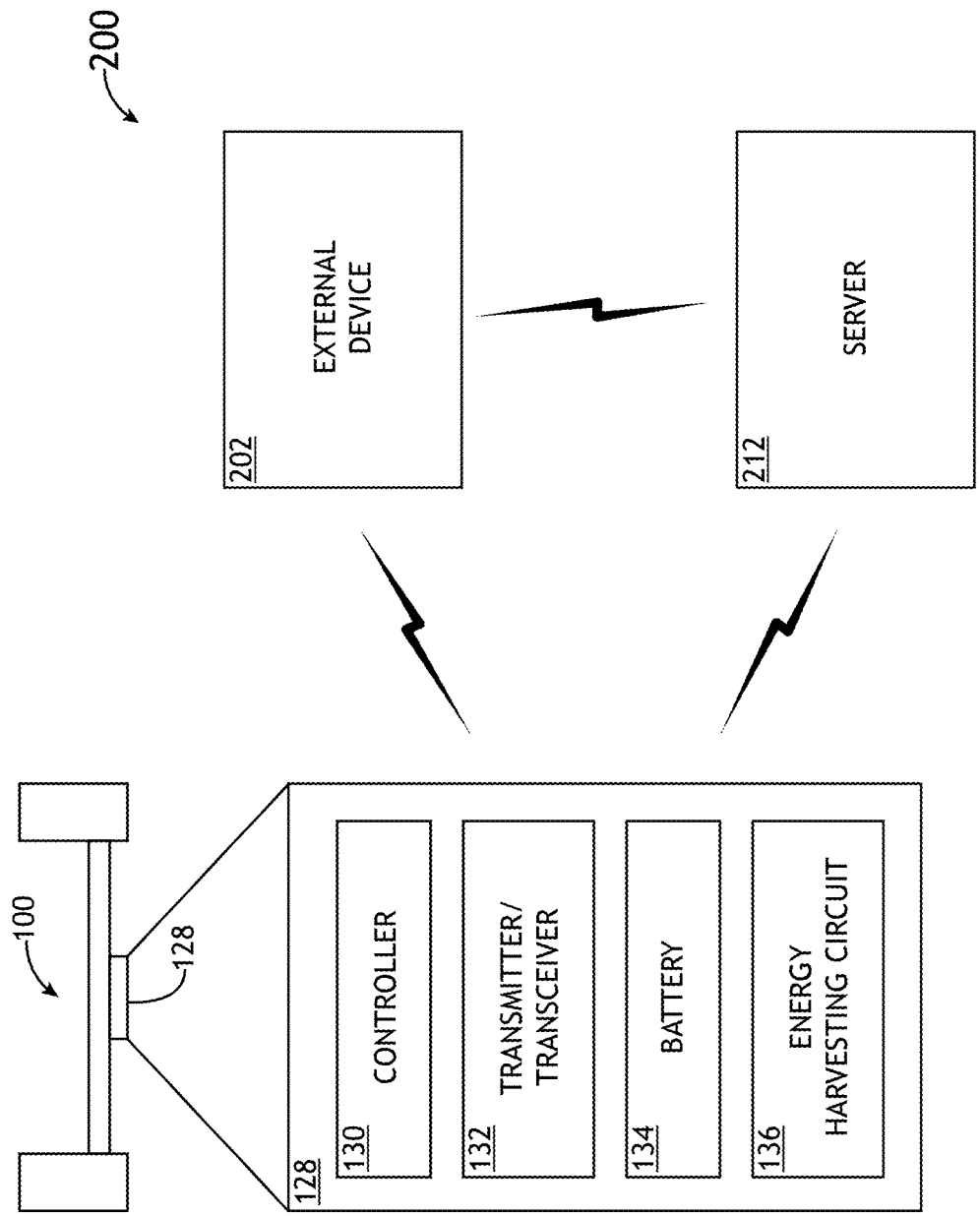
FIG. 8 is another block diagram of an information system that includes a corrective alignment foot brace with sensory electronics, wherein the corrective alignment foot brace includes an onboard electronics assembly for onboard control and/or communication capabilities, in accordance with one or more embodiments of this disclosure.

In some embodiments, the sensor module(s) 106A, 106B, and/or 106 include data cables 110A, 110B, and/or 110 or wires for relaying measurement signals from the sensor modules to an external device. For example, FIG. 7 illustrates a power source, driver and signal conditioning and/or processing (information) system 200 that includes the smart foot brace 100 in communication with an external device 202, such as a desktop computer, notebook computer, mobile device (e.g., smartphone, tablet, smart wearable device, etc.), or any other external device with communication and data processing power. The smart foot brace 100 may be coupled to the external device by wires/cables as described above. Alternatively, as shown in FIG. 8, the smart foot brace 100 may be configured to communicate with the external device 202 or with a receiver or server 212 (e.g., a wireless smart phone, local wireless hub, server, an internet server, a cloud computing network, etc.) through the use of a wireless transmitter or transceiver.

As shown in FIG. 7, the external device 202 may include a processor 204, memory 206, and communication interface 208.

The processor 204 may be miniaturized and be accommodate on board the bar 100, or outside it as shown in FIG. 7, provides a power source, driving, signal conditioning and processing functionality for the onboard force/moment sensors or the external device 202 and can include any number of processors, microprocessors, microcontrollers, circuitry, field programmable gate array (FPGA) or other processing systems and resident or external memory for storing data, executable code and other information accessed or generated by the external device 202. The processor 204 can execute one or more software programs embodied in a non-transitory computer readable medium (e.g., memory 206) that implement techniques/operations described herein. The processor 204 is not limited by the materials from which it is formed, or the processing mechanisms employed therein and, as such, can be implemented via semiconductor(s) and/or transistors (e.g., using electronic integrated circuit (IC) components), and so forth.

The memory 206 can be an example of tangible, computer-readable storage medium that provides storage functionality to store various data and/or program code associated with operation of the external device 202/processor 204, such as software programs and/or code segments, or other data to instruct the processor 204, and possibly other components of the external device 202, to perform the functionality described herein. Thus, the memory 206 can store data, such as a program of instructions for operating the external device 202, including its components (e.g., processor 204, communication interface 206, user interface 208, etc.), and so forth. It should be noted that while a single memory is described, a wide variety of types and combinations of memory (e.g., Solid state, ROM, EPROM, EEPROM, tangible, non-transitory memory) can be employed. The memory 206 can be integral with the processor 204, can comprise stand-alone memory, or can be a combination of both. Some examples of the memory 206 can include removable and non-removable memory components, such as random-access memory (RAM), read-only memory (ROM), flash memory (e.g., a secure digital (SD) memory card, a mini-SD memory card and/or a micro-SD memory card), solid-state drive (SSD) memory, magnetic memory, optical memory, universal serial bus (USB) memory devices, hard disk memory, external memory, or the like.

The communication interface 208 can be operatively configured to communicate with components of the external device 202. For example, the communication interface 208 can be configured to retrieve data from or send data to the processor 204 or other devices (e.g., the sensor module(s) 106A, 106B, and/or 106, actuator(s) 122A and/or 122B, server 212, controller 130, etc.), transmit data for storage in the memory 206, retrieve data from storage in the memory 206, and so forth. The communication interface 208 can also be communicatively coupled with the processor 204 to facilitate data transfer between components of the external device 202 and the processor 204. It should be noted that while the communication interface 208 is described as a component of the external device 202, one or more components of the communication interface 208 can be implemented as external components communicatively coupled to the external device 202 via a wired and/or wireless connection. In embodiments, the communication interface 208 may also include or may be coupled with a transmitter, receiver, transceiver, physical connection interface, or any combination thereof.

The external device 202 can also include and/or connect to one or more user interface devices 210 (e.g., via the communication interface 208), such as an input device (e.g., a trackpad, a touchpad, a touchscreen, a keyboard, a keypad, a microphone (e.g., for voice commands), etc.) and/or an output device (e.g., LED status lights, a miniature screen display, a speaker, a tactile feedback device, etc.).

It shall be understood that any of the functions, steps or operations described herein are not necessarily all performed by one external device 202. In some embodiments, various functions, steps, or operations may be performed by one or more external devices 202. In this regard, the "external device 202" may sometimes refer to a plurality of external devices. For example, one or more operations and/or sub-operations may be performed by a first external device, additional operations and/or sub-operations may be performed by a second external device, and so forth. Furthermore, some of the operations and/or sub-operations may be performed in parallel and not necessarily in the order that they are disclosed herein.

In some embodiments, the external device 202 is configured to receive and process measurement signals from the sensor module(s) 106A, 106B, and/or 106 of the smart foot brace 100 through the use of one or more data cables/wires (e.g., data cable(s) 110A, 110B, and/or 110). In advanced embodiments, the smart foot brace 100 includes an onboard electronics assembly 128, as shown in FIG. 8. The onboard electronics assembly 128 may include a controller 130 that is communicatively coupled to the sensor module(s) 106A, 106B, and/or 106. The controller 130 may comprise any on-board electronic interface instrument, driver, or controller. The controller 130 may be configured to drive, condition, process, record, and/or analyze the sensor data digital or analog signals. The controller 130 may be additionally or alternatively configured to communicate the sensor data to external sources (e.g., to an external device 202, local/remote server 212, etc.). In even more advanced embodiments, the controller 130 may also be communicatively coupled to one or more actuators (e.g., actuator(s) 122A and/or 122B, or additional actuators not shown such as piezo electric inch motors or similar) and configured to implement adjustments to brace alignment and/or stiffness parameters by controlling the one or more actuators.

The controller 130 may be a microcontroller or any programmable device that includes a processor and memory. The processor provides processing functionality for at least the controller and can include any number of processors, microprocessors, microcontrollers, circuitry, field programmable gate array (FPGA) or other processing systems and resident or external memory for storing data, executable code and other information accessed or generated by the controller. The processor can execute one or more software programs embodied in a non-transitory computer readable medium (e.g., memory) that implement techniques/operations described herein. The processor is not limited by the materials from which it is formed, or the processing mechanisms employed therein and, as such, can be implemented via semiconductor(s) and/or transistors (e.g., using electronic integrated circuit (IC) components), and so forth.

The memory can be an example of tangible, computer-readable storage medium that provides storage functionality to store various data and/or program code associated with operation of the controller 130, such as software programs and/or code segments, or other data to instruct the processor, and possibly other components of the controller 130, to perform the functionality described herein. Thus, the memory can store data, such as a program of instructions for operating the controller 130, including its components. It should be noted that while a single memory is described, a wide variety of types and combinations of memory (e.g., tangible, non-transitory memory) can be employed. The memory can be integral with the processor, can comprise stand-alone memory, or can be a combination of both. Some examples of the memory can include removable and non-removable memory components, such as random-access memory (RAM), read-only memory (ROM), flash memory (e.g., a secure digital (SD) memory card, a mini-SD memory card and/or a micro-SD memory card), solid-state drive (SSD) memory, magnetic memory, optical memory, universal serial bus (USB) memory devices, hard disk memory, external memory, or the like.

It shall be understood that any of the functions, steps or operations described herein are not necessarily all performed by one controller 130. In some embodiments, various functions, steps, or operations may be performed by one or more controllers 130. For example, one or more operations and/or sub-operations may be performed by a first controller, additional operations and/or sub-operations may be performed by a second controller, and so forth. In this regard, the "controller 130" may sometimes refer to a plurality of controllers. Furthermore, some of the operations and/or sub-operations may be performed in parallel and not necessarily in the order that they are disclosed herein.

The onboard electronics assembly 128 may further include or may be coupled to a wireless transmitter/transceiver 132 for communications between the controller 130 and other devices (e.g., external device 202, server 212, etc.). In some embodiments, the onboard electronics assembly 128/controller 130 also includes a communication interface for connecting to an onboard/external user interface device, such as an input device (e.g., a trackpad, a touchpad, a touchscreen, a keyboard, a keypad, a microphone (e.g., for voice commands), etc.) and/or an output device (e.g., a display, a speaker, a tactile feedback device, etc.).

The onboard electronics assembly 128 may be powered by an internally or externally located battery 134 or another type of energy storage device (e.g., supercapacitor). In some embodiments, the battery 134/energy storage device is rechargeable. In this case, the onboard electronics assembly 128 may further include or may be coupled to an energy harvesting circuit 136, such as, but not limited to, an electric charging circuit, an inductive charging circuit, a piezoelectric power generator, or a solar cell. Any of the brace sensor electronics and signal conditioning functions can be powered on board by rechargeable or conventional batteries, or by remote wireless (e.g. electro-inductive) charging, or even powered by electronic power (charge) harvested from piezoelectric elements. In advanced embodiments, piezo electric elements are embedded within the smart foot brace 100 (e.g., within the shoes 102A, 102B, coupled to the shoes, or coupled to or near the sensor module(s) 106A, 106B, and/or 106). The piezo electric elements can produce small voltage (charge) when they are strained as part of the bending, torsion or tension/compression of the brace. The harvested piezo electric charge can then be rectified and regulated and stored in capacitors or batteries on board the system to deliver small DC voltage to power the system electronics.

Ancillary electronic devices (e.g., onboard electronics assembly 128, external device 202, etc.) can be on-board the brace or carried by the body of the patient (e.g., wearable or within pockets in clothes) or next to the patient (e.g., crib or bed-side cabinet, etc.) or other locations. The wireless transmission can be done in any protocol including WiFi, Bluetooth, the same through cell phone or other connectivity systems/protocols. The ancillary electronic devices are used for a) providing driving DC voltage power, b) analog and digital conditioning of the sensor module(s) 106A, 106B, and/or 106 from the brace, and c) communication to the outside world including data transfer, logging and in more advanced version remote manual or automatic control of the brace stiffness. In some embodiments, the ancillary electronic device may also be configured to display such data (e.g., on miniature screen local to the patient or on the brace, processing of such, interpretation, and control to produce actions such as on advanced models to control (adjust) the stiffness and functionality of the brace, alert the patient, parent, or caregiver, and so forth.

In some embodiments, the external device 202 is configured to store data collected by the sensor module(s) 106A, 106B, and/or 106. Optionally, the external device 202 may be further configured to upload the sensor data to a server 212. A clinician can then access the sensor data from the server 212 at a later time, via the same external device 202 or another external device 202, or it can be transmitted to another computer/device for additional processing or comparison against sensor data collected from the same patient previously or from other patients.

The external device 202 may optionally be configured to provide an alert (e.g., via communication interface 208 and/or user interface 210) based on the sensor data, for example, when the sensor data includes force or moment measurements outside of a selected range and/or fulfilling certain selective criteria. In an example scenario, the sensor data may include force or moment measurements associated with high physical resistance by the patient. As such, the external device 202 may be configured to provide an alert indicating that the brace parameters should be relaxed to improve tolerance and/or reduce risk of fracture. In another example scenario, the sensor data may include force or moment measurements associate with little to no physical resistance by the patient. As such, the external device 202 may be configured to provide an alert indicated that the brace parameters should be advanced to improve efficacy of the brace.

In more advanced embodiments, the external device 202 may be configured to compute new alignment/stiffness parameters or otherwise determine an adjustment for one or more parameters of the brace (e.g., alignment or stiffness parameters of the first show 102A, second shoe 102B, and/or bar 104) based on the sensor data when the sensor data includes force or moment measurements outside of a selected range and/or fulfilling certain selective criteria. In an example scenario, the sensor data may include force or moment measurements associated with high physical resistance by the patient. As such, the external device 202 may be configured to determine an adjustment to relax one or more stiffness/alignment parameters to improve tolerance and/or reduce risk of fracture. In another example scenario, the sensor data may include force or moment measurements associate with little to no physical resistance by the patient. As such, the external device 202 may be configured to determine an adjustment to relax one or more stiffness/alignment parameters improve efficacy of the brace. In even more advanced embodiments, the external device 202 may be configured to implement an adjustment by controlling the actuator(s) 122A and/or 122B directly or by communicating control signals/instructions to an onboard controller (e.g., controller 130 of onboard electronics assembly 128).

In further embodiments, some or all of the external device 202 functionality described above is implemented by onboard systems (e.g., onboard electronics assembly 128). For example, the onboard electronics assembly 128 may be configured to perform any/all of the following: store and/or process sensor data via controller 130; send the sensor data to the external device 202 or server 212 via wired connection or wireless transmitter/transceiver 132; generate an alert (e.g., transmitter/transceiver 132 and/or an onboard user interface, such as a display, indicator light, or speaker/audible alarm system) based on the sensor data when the sensor data includes one or more force or moment measurements outside of a specified range; determine an adjustment for one or more parameters of the brace (e.g., alignment or stiffness parameters of the first show 102A, second shoe 102B, and/or bar 104) based on the sensor data when the sensor data includes force or moment measurements outside of a selected range; and/or implement an adjustment for one or more brace parameters by controlling implement an adjustment by controlling the actuator(s) 122A and/or 122B.

Figure 9B:
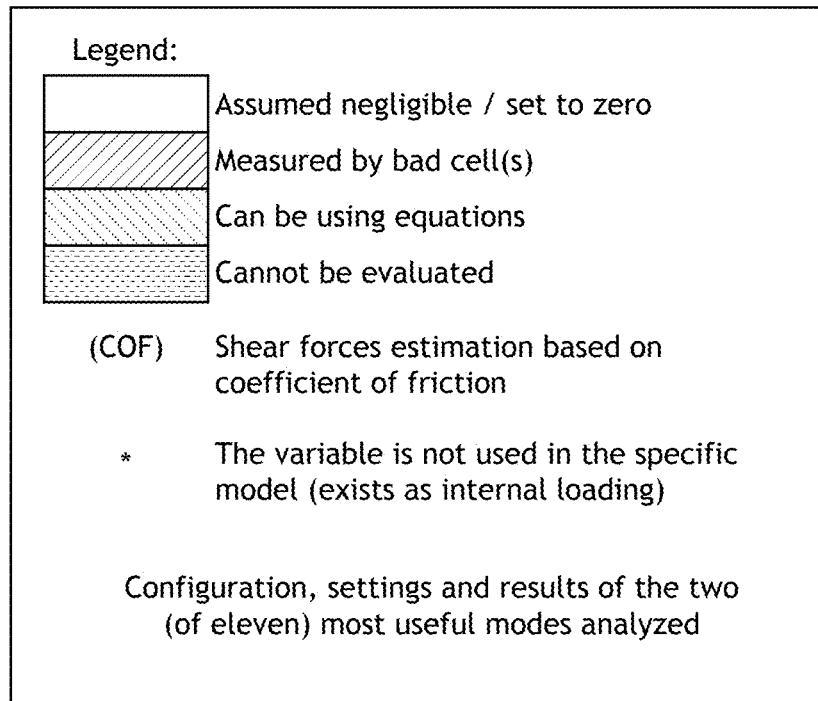
FIG. 9B is a legend for the table in FIG. 9A.

Referring now to FIGS. 9A and 9B, the inventors have performed analysis and testing in the course of planning optimized sensor module configurations for the smart foot brace 100. In the analysis and testing, the use of one or two load cell sensors were modeled, each with 6 DOF in various configurations. A total of 11 analytical models were considered using various combinations of the following situations and assumptions: The number of load cell(s) (one or two) to be used, and their location in the system, whether the child is in bed and if the bed supports the brace under the feet or not, and the detail of how the bed support reacts to the system. The latter could be represented either as a solely compressive reaction, i.e., perpendicular to the bars and to the tibial axes, or to contain shear/friction components, i.e., forces in the plane of the bed surface. FIGS. 9A and 9B present abridged results from the inventors' analysis on what can be directly measured or determined by data processing in two of the most sophisticated configurations and assumptions, using two 6-degree of freedom force/moment sensors and with bed support touching the bar in one configuration and touching the shoe in the other. The overall analysis (beyond what is shown in FIGS. 9A and 9B) determined all the possible configurations to evaluate the loading (contribution) of the brace to the whole system (child), and the ability to differentiate forces originating from each of the two feet. One resulting system (with two sensor modules) was then modeled further to determine the effects of where the bed support should contact the brace as the child lies supine, at the bar/brace (model 3c) or at the shoe (model 4a). These preliminary data suggested a custom brace containing two 6 DOF load cells housed such that the bed supports the bar (and not the shoes), allowing measurement of all forces and moments in the legs (model 3c). The alternative, (model 4a), allows all the forces and moments transmitted by the bar to be measured, hence representing the total bar action. Therefore, a system that allows the bed supports to be reconfigurable would help optimize all the desired measurements. On the other hand, much simpler or more advanced systems can be configured with one or more load cells/force sensors as discussed throughout this disclosure.

In simpler embodiments, the smart foot brace 100 includes a shoe (e.g., 102A/102B) that can be adjustably oriented in terms of its alignment relative to any anchoring mechanism (e.g., bar 104, a platform, a leg brace (on same or other leg), a bed, etc.) with a sensor module (e.g., sensor module 106A/106B) coupled to the shoe and/or the anchoring mechanism. In some embodiments, the sensor module may be located between the shoe and the anchoring mechanism. The sensor module can measure force and/or moment along one or more axes as described above. The sensor module may detect forces exerted by one foot to the shoe and vice versa, forces exerted by the shoe to the anchoring mechanism and vice versa, external forces from a bed or floor, a subset or all of the forementioned forces, and any other internal/external forces acting on the brace.

Although the technology has been described with reference to the embodiments illustrated in the attached drawing figures, equivalents may be employed, and substitutions may be made herein without departing from the scope of the technology as recited in the claims. Components illustrated and described herein are examples of devices and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A corrective alignment foot brace, comprising:
    a first shoe;
    a second shoe;
    a bar rigidly or semi-rigidly connecting the first shoe and the second shoe, wherein the first shoe can be adjustably oriented in terms of its alignment relative to the second shoe and relative to the bar; and
    a sensor module coupled to at least one of the first shoe, the second shoe, or the bar, the sensor module configured to detect at least one force or moment acting on the sensor module along or about at least one axis, wherein the sensor module is coupled to the first shoe, and wherein the sensor module is coupled in between the first shoe and the bar.

2. The corrective alignment foot brace of claim 1, further comprising:
    an onboard controller configured to condition signals, and store data collected by the sensor module.

3. The corrective alignment foot brace of claim 2, further comprising:
    a battery configured to power the onboard controller.

4. The corrective alignment foot brace of claim 3, further comprising:
    an onboard energy harvesting circuit configured to charge the battery, wherein the onboard energy harvesting circuit comprises at least one of an electric charging circuit, an inductive charging circuit, a piezoelectric power generator, or a solar cell.

5. The corrective alignment foot brace of claim 2, further comprising:
    a wireless transmitter or wired connection configured to send the data collected by the sensor module to an external device.

6. The corrective alignment foot brace of claim 2, wherein the on-board controller is configured to generate an alert based on the data collected by the sensor module when the data includes one or more force or moment measurements outside of a specified range or fulfilling certain selective criteria.

7. The corrective alignment foot brace of claim 1, wherein the sensor module is in communication with an external device that is configured to store data collected by the sensor module.

8. The corrective alignment foot brace of claim 7, wherein the external device is configured to upload the data collected by the sensor module to a server.

9. The corrective alignment foot brace of claim 7, wherein the external device is configured to provide an alert based on the data collected by the sensor module when the data includes force or moment measurements outside of a selected range or fulfilling certain selective criteria.

10. The corrective alignment foot brace of claim 7, wherein the external device is configured to determine an adjustment for a parameter of the first shoe, the second shoe, or the bar based on the data collected by the sensor module when the data includes force or moment measurements outside of a selected range or fulfilling certain selective criteria.

11. The corrective alignment foot brace of claim 1, wherein the sensor module comprises a multiple axis sensor configured to detect a plurality of forces or moments acting on the sensor module along or about a plurality of axes.

12. The corrective alignment foot brace of claim 1, further comprising:
    a second sensor module coupled to the second shoe.

13. The corrective alignment foot brace of claim 1, further comprising:
    one or more adjustable, tunable or interchangeable stiffness elements with selected stiffness or tension parameters based on data collected by the sensor module, the one or more tunable or interchangeable stiffness elements configured to act on at least one of the first shoe or the second shoe or within the bar.

14. A corrective alignment foot brace, comprising:
a first shoe;
a second shoe;
a bar rigidly or semi-rigidly connecting the first shoe and the second shoe, wherein the first shoe can be adjustably oriented in terms of its alignment relative to the second shoe and relative to the bar;
a sensor module coupled to at least one of the first shoe, the second shoe, or the bar, the sensor module configured to detect at least one force or moment acting on the sensor module along or about at least one axis; and
an onboard controller configured to condition signals, and store data collected by the sensor module, wherein the onboard controller is configured to determine an adjustment for a parameter of the first shoe, the second shoe, or the bar based on the data collected by the sensor module when the data includes force or moment measurements outside of a selected range or fulfilling certain selective criteria.

15. The corrective alignment foot brace of claim 14, wherein the on-board controller is further configured to implement the adjustment by controlling at least one actuator coupled to at least one of the first shoe, the second shoe, or the bar.

16. A corrective alignment foot brace, comprising:
a first shoe;
a second shoe;
a bar rigidly or semi-rigidly connecting the first shoe and the second shoe, wherein the first shoe can be adjustably oriented in terms of its alignment relative to the second shoe and relative to the bar; and
a sensor module coupled to at least one of the first shoe, the second shoe, or the bar, the sensor module configured to detect at least one force or moment acting on the sensor module along or about at least one axis, wherein the sensor module comprises a multiple axis sensor configured to detect a plurality of forces or moments acting on the sensor module along or about a plurality of axes, and wherein the sensor module is coupled to the bar in between the first shoe and the second shoe.

17. A corrective alignment foot brace, comprising:
a first shoe;
a second shoe;
a bar rigidly or semi-rigidly connecting the first shoe and the second shoe, wherein the first shoe can be adjustably oriented in terms of its alignment relative to the second shoe and relative to the bar;
a sensor module coupled to at least one of the first shoe, the second shoe, or the bar, the sensor module configured to detect at least one force or moment acting on the sensor module along or about at least one axis, wherein the sensor module is coupled to the first shoe; and
an adapter for coupling the sensor module to the first shoe, wherein the adapter is configured to interface with the first shoe via a coupling interface for a plurality of interchangeable shoes to accommodate different shoe sizes and designs.

18. A corrective alignment foot brace, comprising:
a first shoe;
a second shoe;
a bar rigidly or semi-rigidly connecting the first shoe and the second shoe, wherein the first shoe can be adjustably oriented in terms of its alignment relative to the second shoe and relative to the bar;
a sensor module coupled to at least one of the first shoe, the second shoe, or the bar, the sensor module configured to detect at least one force or moment acting on the sensor module along or about at least one axis; and
a configurable bed support shield for controlling which part of the sensor module bears forces between the sensor module and a bed.

19. A corrective alignment foot brace, comprising:
a first shoe;
a second shoe;
a bar rigidly or semi-rigidly connecting the first shoe and the second shoe, wherein the first shoe can be adjustably oriented in terms of its alignment relative to the second shoe and relative to the bar, wherein the bar comprises a plurality of modular elements that can be added or removed to change a stiffness or tension parameter of the bar; and
a sensor module coupled to at least one of the first shoe, the second shoe, or the bar, the sensor module configured to detect at least one force or moment acting on the sensor module along or about at least one axis.

* * * * *